United States Patent [19]

Mueller et al.

[11] 4,345,094

[45] * Aug. 17, 1982

[54] PROCESS FOR THE PRODUCTION OF 6-HYDROXY-2-NAPHTHOIC ACID

[75] Inventors: Michael J. Mueller, Parkersburg, W. Va.; Carroll S. Montgomery, Somerville, N.J.

[73] Assignee: American Cyanamid Company, Stamford, Conn.

[*] Notice: The portion of the term of this patent subsequent to Sep. 1, 1998, has been disclaimed.

[21] Appl. No.: 269,075

[22] Filed: Jun. 2, 1981

Related U.S. Application Data

[62] Division of Ser. No. 127,703, Mar. 6, 1980, Pat. No. 4,287,357.

[51] Int. Cl.$^3$ ............................................. C07C 51/15

[52] U.S. Cl. ................................... 562/425; 562/423; 562/424

[58] Field of Search ....................... 562/425, 423, 424

[56] References Cited

U.S. PATENT DOCUMENTS 4,287,357  9/1981  Mueller et al. ...................... 562/425

Primary Examiner—Alan Siegel
Attorney, Agent, or Firm—Frank M. Van Riet; Bruce F. Jacobs

[57] ABSTRACT

The production of 6-hydroxy-2-naphthoic acid from anhydrous potassium 2-naphthoxide and carbon dioxide is improved by forming a mixture of 0.8–1.2 moles of 2-hydroxynaphthalene per equivalent of potassium base, dehydrating the mixture, adding carbon dioxide at about 20 to 90 psi at about 255°–280° C. and agitating and heating it at said pressure and temperature.

3 Claims, No Drawings

PROCESS FOR THE PRODUCTION OF 6-HYDROXY-2-NAPHTHOIC ACID

CROSS-REFERENCE TO RELATED APPLICATIONS

This application is a divisional of our copending application, Ser. No. 127,703, filed Mar. 6, 1980 now U.S. Pat. No. 4,287,357 and entitled PROCESS FOR THE PRODUCTION OF 6-HYDROXY-2-NAPTHOIC ACID.

The present invention relates to a process for the preparation of 6-hydroxy-2-naphthoic acid, more particularly, by the carboxylation of the potassium salt of 2-hydroxynaphthalene with carbon dioxide. Still more particularly, the invention relates to an improved process for the preparation of 6-hydroxy-2-naphthoic acid in which said potassium salt is reacted with carbon dioxide under specific conditions of temperature, pressure, and ratios of reactants which results in increased yield of the desired product.

The production of 6-hydroxy-2-naphthoic acid, an intermediate useful for the preparation of synthetic fibers, and structural plastics, by the reaction of the potassium salt of 2-hydroxynaphthalene and carbon dioxide at an elevated temperature, is disclosed by Andre in U.S. Pat. No. 1,593,816. Andre, however, does not disclose the criticality of temperature, pressure, or ratios of reactants. Moreover, upon repeating Andre's work, the actual yield of 6-hydroxy-2-naphthoic acid obtained was found to be only about one-third of the yield reported by Andre. (See Example 6 below).

The carboxylation of alkali metal salts of phenols with carbon dioxide to form acids containing phenolic substituents, the well-known Kolbe-Schmitt reaction, is also disclosed in U.S. Pat. Nos. 3,816,521 and 3,405,169.

In the carboxylation of the potassium salt of 2-hydroxynaphthalene, the initial product formed is 3-hydroxy-2-naphthoic acid which subsequently rearranges in situ to form 6-hydroxy-2-naphthoic acid. It has been found that the conditions which favor the formation of 3-hydroxy-2-naphthoic acid in the Kolbe-Schmitt reaction hinder the rearrangement rection.

There is a need, therefore, for an improved process for the preparation of 6-hydroxy-2-naphthoic acid which will optimize the ratio of 6-hydroxy-2-naphthoic acid to 3-hydroxy-2-naphthoic acid in the reaction product.

SUMMARY OF THE INVENTION

In accordance with the present invention, there is provided an improved process for preparing 6-hydroxy-2-naphthoic acid by reacting essentially anhydrous potassium 2-naphthoxide with carbon dioxide at an elevated temperature, and recovering 6-hydroxy-2-naphthoic acid therefrom, the improvement comprising forming a mixture of 2-hydroxynaphthalene and a potassium base, using about 0.8 to 1.2 moles of 2-hydroxynaphthalene per equivalent of potassium base; dehydrating said mixture; introducing carbon dioxide into said dehydrated mixture at about 20 to 90 psi at about 225° C. to 280° C., while agitating said mixture in a pressure reactor; and heating said stirred mixture of said temperature and under said pressure until the ratio of 6-hydroxy-2-naphthoic acid to 3-hydroxy-2-naphthoic acid in the reaction mixture is at least 2, before recovering said 6-hydroxy-2-naphthoic acid.

In the preferred embodiment, the reaction mixture of potassium 2-naphthoxide and carbon dioxide also contains a non-polar organic flux. In the especially preferred embodiment, the flux is a mixture of isopropylnaphthalenes.

The improved process of the present invention affords the following advantages:

1. A higher yield of 6-hydroxy-2-naphthoic acid is obtained.
2. The high ratio of 6-hydroxy-2-naphthoic acid to 3-hydroxy-2-naphthoic acid obtained improves the recovery yield and purity of the product.
3. The use of a flux improves heat and mass transfer rates thus reducing time cycles and improving the yield.

In carrying out the improved process of the present invention, 2-hydroxynaphthalene and a potassium base are mixed in amounts sufficient to provide a ratio of about 0.8 to 1.2 moles of 2-hydroxy-naphthalene per equivalent of potassium base, and the reaction mixture is dehydrated by distillation, or by passing it through a dehydration apparatus.

Suitable potassium bases include potassium hydroxide, potassium carbonate, potassium hydride, potassium amide, and the like, as well as mixtures thereof. The preferred potassium base is potassium hydroxide with or without potassium carbonate.

Preferably, the potassium base and 2-hydroxynaphthalene are mixed in the presence of a non-polar organic flux to form the potassium 2-naphthoxide and the reaction mixture is dehydrated by distillation under nitrogen until essentially all of the water is removed.

Preferably, in forming the reaction mixture about 1.0 to 1.1 moles of 2-hydroxynaphthalene, and most preferably, about 1.02 to 1.04 moles, are used per mole of potassium base. A large excess of 2-hydroxynaphthalene, for example, about 1.5 moles per mole of potassium hydroxide, has been found to produce a large decrease in the yield of the final product.

It has been found that higher yields may be obtained when a flux is used. As used herein, the term "flux" defined as any non-polar organic material which is not a solvent for the reactants and which is a liquid under the reaction conditions employed. Suitable materials which may be used as a flux include the following:

1-isopropylnaphthalene,
2-isopropylnaphthalene,
naphthalene,
kerosene, and the like.

The preferred flux is a mixture of 1-, and 2-isopropylnaphthalene. Preferably, the dehydrated mixture contains about one part by weight of potassium 2-naphthoxide per part by weight of the mixed isopropylnaphthalenes.

The dehydrated mixture is charged to a pressure reactor, preferably with additional flux and purged with carbon dioxide. The reactor is then sealed and heated at about 255° C. to 285° C., preferably about 260° C. to 280° C., more preferably about 260° C. to 270° C., under a carbon dioxide pressure of about 20 psi to 90 psi, preferably about 30 psi to 80 psi, more preferably about 40 psi to 60 psi, while stirring the reaction mixture vigorously, until analysis of an aliquot of the reaction mixture shows a molecular ratio of 6-hydroxy-2-naphthoic acid to 3-hydroxy-2-naphthoic acid of at least 2, preferably more than 3, and most preferably more than 6. The agitation must be sufficient to ensure the uniform mixing of the carbon dioxide into the reaction mixture, otherwise the carboxylation reaction stops.

At temperatures below 255° C., the reaction product is found to be mainly 3-hydroxy-2-naphthoic acid. Only about a 10% yield of the desired 6-hydroxy-2-naphthoic acid was obtained below 255° C.

At pressures below 40 psi, the yield of 6-hydroxy-2-naphthoic acid decreases. At pressures above 60 psi, the ratio of 6-hydroxy-2-naphthoic acid to 3-hydroxy-2-naphthoic acid decreases.

At temperatures of 280° C., or higher, the reaction time can be critical because of the formation of tars. In carrying out the reaction at 280° C. and 60 psi, the reaction time should be limited to maximize the production of the desired product.

When the raio of 6-hydroxy-2-naphthoic acid to 3-hydroxy-2-naphthoic acid reaches 2, or higher, the reactor is vented to the atmosphere and the reaction mixture is cooled under a nitrogen atmosphere to about 120° C. The reaction mixture is then either diluted with water and/or discharged into water containing enough sulfuric acid to bring the pH of the resulting mixture to 7, or above, preferably about 7.1±0.2.

The aqueous phase of the resulting two-phase liquid mixture is split off from the organic phase at a temperature of about 85°–98° C., preferably about 95° C., and back-extracted twice with an equal volume of an organic flux (even if the flux was not present during the reaction) at the same temperature as the aqueous phase. A buffer, -referably about 0.1 gram of acetic acid per gram of 6-hydroxy-2-naphthoic acid expected, is added to the extracted aqueous phase, and then enough dilute sulfuric acid is added to adjust the pH to about 4.8 to 5.2 to precipitate the 6-hydroxy-2-naphthoic acid. The precipitate may then be recovered by conventional means and dried to obtain the desired 6-hydroxy-2-naphthoic acid in a yield of about 40–60% of theoretical.

The mother liquor obtained on recovery of the product may be treated with additional sulfuric acid to adjust the pH to about 2–4 and precipitate 3-hydroxy-2-naphthoic acid, which may be recovered by filtration.

In the examples which follow, all parts are by weight unless otherwise indicated. All yields are based on potassium base charged. A theoretical yield is defined as one mole of 6-hydroxy-2-naphthoic acid produced for every for every 2 moles of potassium 2-naphthoxide.

EXAMPLE 1

A mixture of 2-hydroxynaphthalene (84 grams; 0.58 mole), 45% potassium hydroxide (70.5 grams; 0.56 mole), and 100 mls of a mixture of 1-, and 2-isopropylnaphthalenes is stirred and heated under a nitrogen atmosphere until 100 mls total of water and isopropylnaphthalene are distilled off. At that point, 100 mls of isopropylnaphthalene is added and the mixture is further heated to distil off an additional 50 mls of isopropylnaphthalene, and obtain a dehydrated mixture.

The dehydrated reaction mixture is cooled to 265° C., charged to a pressure reactor, and purged with carbon dioxide. The reactor is then sealed and pressurized with carbon dioxide to 40 psi while stirring slowly. The rate of stirring is then increased to 1500 rpm and the mixture is stirred at 265° C. under 40 psi of carbon dioxide for 16 hours. The reaction mixture is then cooled to 260° C., vented to atmospheric pressure, and cooled under a nitrogen atmosphere to 120° C. Water is then added to dilute the reaction mixture.

The diluted reaction mixture is discharged into a flask containing 7.5 grams of sulfuric acid in 100 mls of water. The pH of the resulting mixture is then adjusted to 7.0±1 with sulfuric acid, and the two-phase liquid mixture is heated to 95° C. while stirring. The mixture is allowed to settle, the layers are split apart, and the aqueous phase is washed twice with 100-ml portions of isopropylnaphthalene. The isopropylnaphthalene-washed aqueous phase is then stirred at 65°–75° C. and 20 grams of a 15% by weight solution of acetic acid in water is added thereto. Sulfuric acid (15 grams of sulfuric acid per 100 mls of solution) is then added over a period of 15 to 30 minutes until the pH of the resulting slurry is 4.8 to 5.2. The slurry is then cooled to 25°–35° C. and filtered. The resulting filter cake is then washed with water and dried to obtain 27.4 grams (54% of theoretical) of 6-hydroxy-2-naphthoic acid.

The aqueous mother liquor is adjusted to pH 2.5 with dilute sulfuric acid and the resulting precipitate is collected by filtration, washed, and dried to afford a mixture containing 1.6 grams of 6-hydroxy-2-naphthoic acid and 2.9 grams of 3-hydroxy-2-naphthoic acid.

The combined organic phases contain 50.2 grams of 2-hydroxynaphthalene, which can be recovered and recycled.

In the manner described above, carrying out the reaction at 80 psi, and 100 psi, the yields of 6-hydroxy-2-naphthoic acid obtained are 49.7%, and 26.8%, respectively.

The above example illustrates the present invention as well as the effect of increased pressure on the yield of 6-hydroxy-2-naphthoic acid.

EXAMPLE 2

The procedure of Example 1 is followed in every detail except that a mixture of 2-hydroxynaphthalene (83 grams; 0.576 mole), 45% potassium hydroxide (69.7 grams; 0.559 mole), and potassium carbonate (20 grams; 0.145 mole) is employed initially, the dehydrated reaction mixture is heated under 60 psi of carbon dioxide for 10 hours, and the aqueous phase is washed twice with 100-ml portions of isopropylnaphthalene at 85°–95° C. There is obtained 25.5 grams of 6-hydroxy-2-naphthoic acid (48.1% of theoretical), and 4.6 grams of 3-hydroxy-2-naphthoic acid.

EXAMPLE 3

The procedure of Example 2 is followed in every detail except that no potassium carbonate is used. There is obtained 23.7 grams (44.5% of theoretical) of 6-hydroxy-2-naphthoic acid, and 4.8 grams of 3-hydroxy-2-naphthoic acid.

EXAMPLE 4

The procedure of Example 1 is followed in every detail except that the reaction mixture is heated at 265° C. in a pressure reactor for 16 hours under a pressure of 60 psi. There is obtained 36.6 grams (49.5% of theoretical) of 6-hydroxy-2-naphthoic acid. The yield of 3-hydroxy-2-naphthoic acid is 7.5%. The ratio of 6-hydroxy-2-naphthoic acid to 3-hydroxy-2-naphthoic acid is 6.6 to 1.

Carrying out the reaction described above, at 250° C. for 16 hours under a pressure of 60 psi, affords only 11.5 grams (15.5% of theoretical) of 6-hydroxy-2-naphthoic acid. The yield of 3-hydroxy-2-naphthoic acid is 53.6%.

The above example illustrates the decreases in the yield of 6-hydroxy-2-naphthoic acid of 6-hydroxy-2-naphthoic acid to 3-hydroxy-2-naphthoic acid obtained when the temperature is reduced below 255° C.

EXAMPLE 5

A mixture of 2-hydroxynaphthalene (116 grams; 0.80 mole), and 45% potassium hydroxide (97.8 grams; 0.78 mole), is stirred and heated under nitrogen until distillation stops and the temperature rises to 275° C. The mixture is then cooled to 270° C. and held under a fast stream of nitrogen for 30 minutes. The mixture is then further cooled to 265° C. and purged with carbon dioxide while stirring rapidly.

The reaction mixture is placed in a pressure reactor, and the reactor is sealed and pressurized with carbon dioxide to 60 psi. The reaction mixture is then stirred at 600 rpm and 265° C. for 11 hours under a pressure of 60 psi. The reactor is then vented to atmospheric pressure, and cooled under a nitrogen atmosphere to 120° C. The reaction mixture is then processed as described in Example 2. There is obtained 29.0 grams (39.3% of theoretical) of 6-hydroxy-2-naphthoic acid and 6.0 grams (8.2% of theoretical) of 3-hydroxy-2-naphthoic acid.

The above example illustrates the process of the present invention carried out without a flux.

EXAMPLE 6

The procedure of Example 5 is followed in every detail except that the reaction mixture is heated at 230° C. ±5° C. for 18.5 hours. The yield of 6-hydroxy-2-naphthoic acid obtained is only 19.5% of theoretical, whereas the yield of 3-hydroxy-2-naphthoic acid is 37.6% of theoretical.

The above example represents the process of Andre carried out under conditions which should have maximized the yield of 6-hydroxy-2-naphthoic acid. It is obvious from these results that the process of Andre neither affords a high yield of 6-hydroxy-2-naphthoic acid, nor a high ratio of 6-hydroxy-2-naphthoic acid to 3-hydroxy-2-naphthoic acid.

A comparison of Example 5 with Example 6 again illustrates the beneficial effect of temperatures above 255° C. on the yield of 6-hydroxy-2-naphthoic acid.

What is claimed is:

1. In a process for preparing 6-hydroxy-2-naphthoic acid by reacting essentially anhydrous potassium 2-naphthoxide with carbon dioxide at an elevated temperature, and recovering 6-hydroxy-2-naphthoic acid therefore, the improvement which comprises forming a mixture of 2-hydroxynaphthalene and a potassium base, using about 0.8 to 1.2 moles of 2-hydroxynaphthalene per equivalent of potassium base; dehydrating said mixture; introducing carbon dioxide into said dehydrated mixture at about 20 psi to 90 psi at about 255° C. to 280° C., while agitating said mixture in a pressure reactor; heating said agitated mixture at said temperature and under said pressure until the ratio of 6-hydroxy-2-naphthoic acid to 3-hydroxy-2-naphthoic acid in the reaction mixture is at least 2, either diluting said reaction mixture with or discharging said reaction mixture into water containing sufficient sulfuric acid to bring the pH to at least 7, thereby form a two-phase mixture; separating the aqueous phase from the organic phase; contacting said aqueous phase with 0.1 gram of acetic acid per gram of expected 6-hydroxy-2-naphthoic acid and additional sulfuric acid to bring the pH to about 4.8–5.2 and recovering said 6-hydroxy-2-naphthoic acid.

2. A process according to claim 1 wherein said aqueous phase is extracted with an organic flux and the resultant extracted aqueous phase is recovered and then contacted with said acetic acid.

3. A process according to claim 1 wherein the mother liquor resulting from the recovery of said 6-hydroxy-2-naphthoic acid is contacted with additional sulfuric acid to bring the pH to about 2–4 and recovering 3-hydroxy-2-naphthoic acid therefrom.

* * * * *